T 864,013

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JULY 29, 1969

864 O.G. 1405

616,479

WATER-INSOLUBLE METHINE COMPOUNDS

Max A. Weaver and David J. Wallace, both of P.O. Box 511, Kingsport, Tenn. 37662

Filed Feb. 16, 1967. Published July 29, 1969
Int. Cl. C07d *99/00, 87/26, 55/00*
U.S. Cl. 260—247.5
No Drawing. 29 Pages Specification

Novel methine compounds having a phenylene or tetrahydroquinoline nucleus and a heterocyclic group of the formula

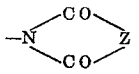

wherein Z represents —NH—NH— or a chain of atoms consisting of carbon and at least one oxygen atom, sulfur atom or nitrogen atom, are useful as dyes for hydrophobic textile materials such as polyester and cellulose acetate fibers. For example, the compound having the formula

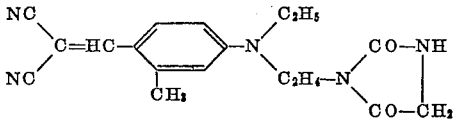

dyes cellulose acetate and polyester fibers bright greenish-yellow shades of excellent fastness properties.